United States Patent [19]
Tanaka et al.

[11] Patent Number: 5,973,151
[45] Date of Patent: Oct. 26, 1999

[54] AROMATIC CONDENSATION COMPOUNDS USEFUL AS OPTICALLY ACTIVE BUILDING BLOCKS

[75] Inventors: Yasutaka Tanaka; Akemi Sekita; Hiroshi Suzuki, all of Hamamatsu; Akiyoshi Torii, Fukuoka, all of Japan

[73] Assignee: Japan Science and Technology Corporation, Honcho, Japan

[21] Appl. No.: 09/032,081

[22] Filed: Feb. 27, 1998

[30] Foreign Application Priority Data

Feb. 28, 1997 [JP] Japan .................................... 9-062063

[51] Int. Cl.$^6$ ................................................. C07D 471/02
[52] U.S. Cl. .................................................... 546/49
[58] Field of Search ................................................. 546/49

[56] References Cited

PUBLICATIONS

D. Hellwinkel et al.: "Eine allgemeine Synthesemethode fur", Dibenso [b,j][x,z]phenanthroline mit x,z=1,7;4,7 and 1,10 . Liebigs Annalen Der Chemie., 1985, Weinheim De. pp. 1501–1507, XP002067630.

W. Borsche et al.: Ober viekernige kondensierte Systeme mit heterocyclischen Ringen. XIII Justus Leibigs Annalen Der Chemie., vol. 550, 1942, Weinheim De, pp. 160–165, XP002067631.

G.M. Badger et al.: "Polynuclear heterocyclic systems. Part V. 5:8–Diazapentaphene."Journal of the Chemical Society., 1952, Letchworth GB, pp. 1874–1877, XP002067632.

Primary Examiner—John Kight
Assistant Examiner—Charanjit S. Aulakh
Attorney, Agent, or Firm—Fay, Sharpe, Beall, Fagan Minnich & McKee

[57] ABSTRACT

Disclosed are aromatic condensation compounds useful as building blocks for construction of various types of optically active substances and reagent, wherein the aromatic condensation compounds are represented by general formula (1) below and capable of forming enantiomeric isomers. In the formula, two Rs are the same or different functional groups and selected from among linear, branched and cyclic hydrocarbon groups of 1–16 carbon atoms, either of which R may be hydrogen. A portion of the aromatic nucleus may be reduced, or at least one of the two nitrogen atoms may be quaternary. The aromatic condensation compounds can be produced by heating and reacting N,N'-diphenyl-p-phenylenediamine with a carboxylic acid represented by the general formula —RCOOH in an amount of at least 2 molar equivalents with respect to the diamine, at 180–210° C. in the presence of a Lewis acid such as zinc chloride.

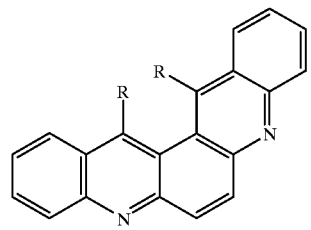

(1)

10 Claims, 3 Drawing Sheets

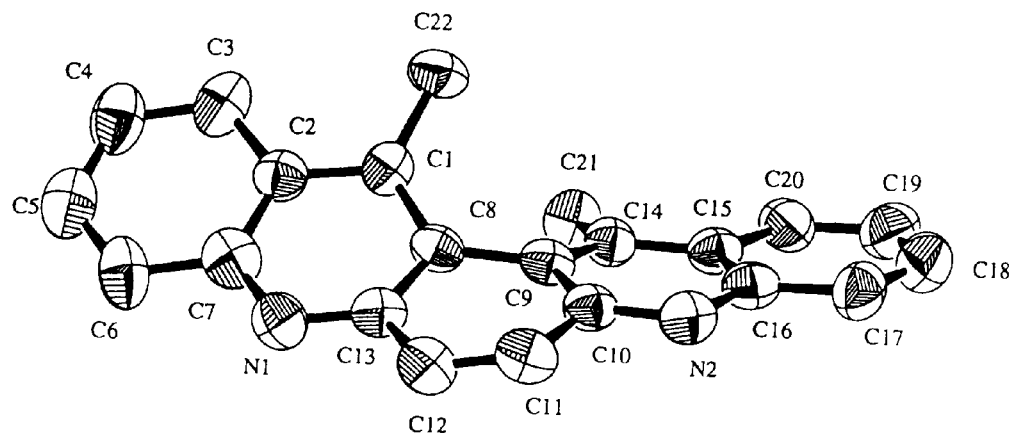
F I G. 4
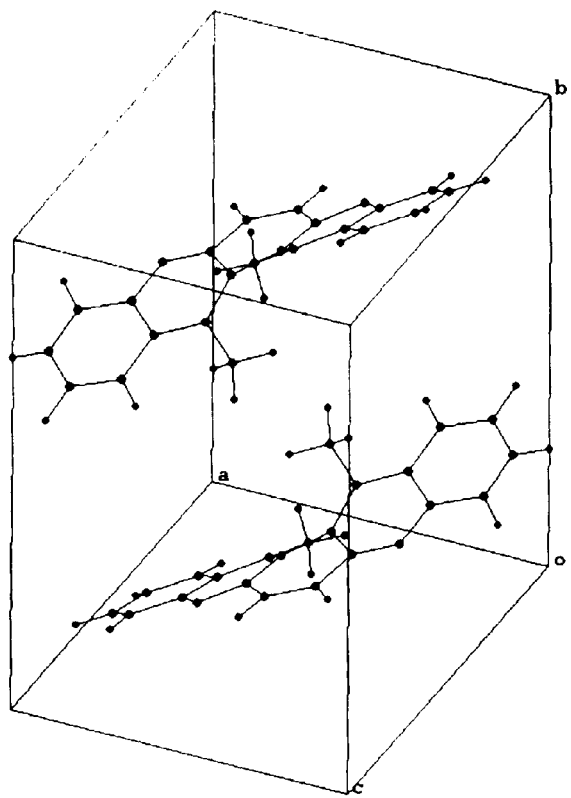
F I G. 5

AROMATIC CONDENSATION COMPOUNDS USEFUL AS OPTICALLY ACTIVE BUILDING BLOCKS

BACKGROUND OF THE INVENTION

1. Field of the Art

The present invention relates to aromatic condensation compounds which form enantiomeric isomers, and more specifically it relates to novel aromatic condensation compounds useful as optically active building blocks for construction of various types of optically active substances, and to a process for their production.

2. Prior Art

Optically active substances which give enantiomeric isomers (hereunder, "enantiomers") which have a relationship often likened to that of the right and left hands, are very important in the development of medicines, foods, agricultural chemicals and aromatics. This is because the physiological activity and chemical reactivity of optically active substances is usually completely different depending on the enantiomer. For example, in the case of glutamic acid, one of the enantiomers (L-form) has flavor while the other enantiomer (D-form) has no flavor. Also, as in the well known thalidomide case, unfortunate drug toxicity was caused by the use of an enantiomer mixture (racemic mixture) including the enantiomer with teratogenicity.

Consequently, in research and development of optically active substances, it is essential to selectively obtain only one enantiomer with the desired physiological activity and chemical reactivity, and optically active substances are used exclusively for this purpose as well. For example, there are known methods wherein a separate optically active substance is added to an enantiomer mixture (racemic mixture) to form a diastereomer, and methods of separating optically active substances (optical separation) using chromatography with the optically active substance supported on a solid phase. Also, research is being ardently pursued using various optically active asymmetric reagents for the purpose of asymmetric synthesis of one optically active enantiomer and asymmetric reduction or oxidation to obtain the desired optically active substance.

A large number of optically active substances (asymmetric molecules or asymmetric compounds) have been discovered toward achieving these purposes, and attempts have also been made at their synthesis by artificial molecular design, but most of these are expected to be asymmetric based on the presence of symmetry elements, with point symmetry or face symmetry. Furthermore, most conventional optically active substances are suited entirely for specific uses, and few can provide useful units as building blocks for constructing various optically active substances. For example, no optically active substances have been found which can be expected to provide materials which function as asymmetric reduction reagents or asymmetric oxidation reagents while also being useful as pharmaceuticals and research reagents by interaction with complicated biological substances such as DNA.

SUMMARY OF THE INVENTION

The present applicant have arrived at the present invention upon the discovery of a novel type of optically active molecule which was unpredictable by the knowledge of the prior art.

Specifically, the present invention provides an aromatic condensation compound characterized by being represented by the following general formula (1):

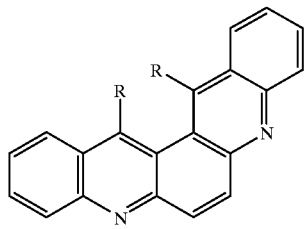

(1)

where each R is the same or a different functional group and selected from among linear, branched and cyclic hydrocarbon groups of 1–16 carbon atoms, either of which R may be hydrogen, and by being capable of forming enantiomeric isomers.

The present invention further provides a process for producing the aromatic condensation compound of formula (1) above, which comprises heating and reacting N,N'-diphenyl-p-phenylenediamine with a carboxylic acid represented by the general formula —RCOOH (R is the same as defined above) in an amount of at least 2 molar equivalents with respect to said diamine, at 180–210° C. in the presence of a Lewis acid.

The aromatic condensation compounds of the invention constitute a novel type of optically active building block based on molecular twisting rather than the conventionally well-known point asymmetry and face asymmetry.

BRIEF DESCRIPTION OF THE DRAWINGS

FIG. 4 is an ORTEP illustration from X-ray structural analysis of an aromatic condensation compound according to the invention.

FIG. 5 is an illustration of a pair of enantiomers extracted from the unit cell of an aromatic condensation compound according to the invention based on X-ray structural analysis.

PREFERRED EMBODIMENT OF THE INVENTION

It cannot be envisioned that the aromatic condensation compounds represented by the above-mentioned formula (1) have this molecular asymmetry based merely on their structural formula. The present inventors first demonstrated that enantiomeric isomers exist among the molecules of formula (1) by analytical means including X-ray structural analysis, supplemented with theoretical chemical methods such as molecular force field calculations and molecular orbital calculations.

Figure 1:
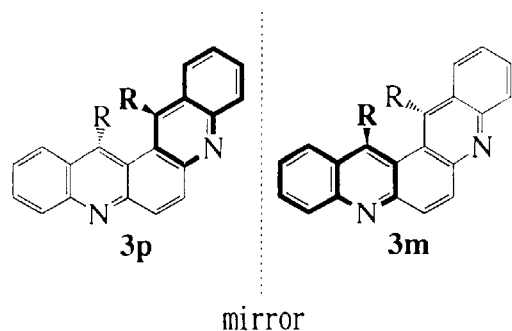
FIG. 1 shows structural formulas for enantiomers of aromatic condensation compounds according to the invention.

That is, as shown in FIG. 1, the aromatic condensation compounds of the invention are molecules which can form a pair of enantiomers comprising a right-handed helical structure (P form: general formula 3p) (R-enantiomer) and a left-handed helical structure (M form: general formula 3m) (S-enanatiomer).

Figure 2:
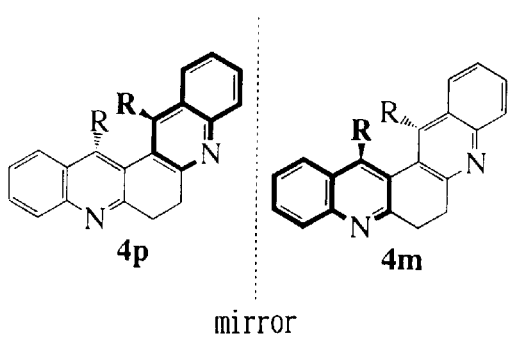
FIG. 2 shows structural formulas for enantiomers of aromatic condensation compounds according to the invention of which a portion of the aromatic nuclei are reduced.
Figure 3:
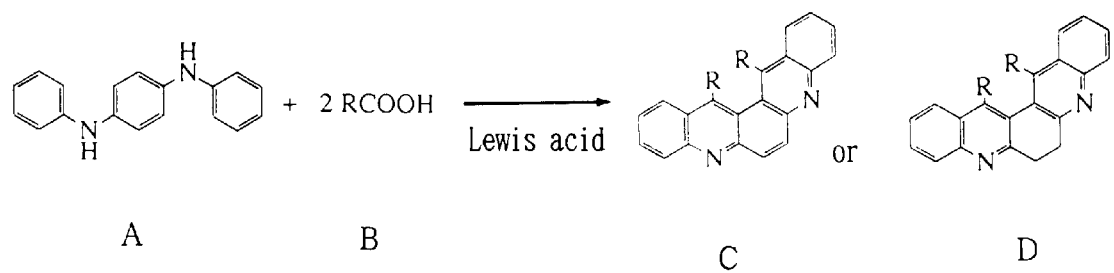
FIG. 3 shows a reaction scheme for production of aromatic condensation compounds according to the invention.

Moreover, the present inventors found that the molecules (compounds) of formula (1) can be obtained by heating and condensation reaction of N,N'-diphenyl-p-phenylenediamine (A) with a carboxylic acid (B) represented by the general formula —RCOOH in an amount of at least 2 molar equivalents with respect to the diamine in the presence of a Lewis acid, according to the reaction scheme shown in FIG. 3, and also found that by adjustment of the reaction conditions it is possible to easily obtain molecules (D) of which part of the aromatic nucleus of compound (C) is reduced, i.e. the molecules represented in FIG. 2.

In the aromatic condensation compounds represented by formula (1), the two Rs are generally the same functional group, but they may also be different functional groups. The functional groups are selected from linear, branched linear and cyclic (alicyclic or aromatic cyclic) hydrocarbon groups of 1–16, and preferably 1–8, carbon atoms. Either R may also be hydrogen.

Preferred examples of functional groups for R include saturated and unsaturated aliphatic hydrocarbon groups such as methyl, ethyl, propyl, isopropyl, butyl, isobutyl, t-butyl, pentyl, isopentyl, neopentyl, hexyl, propenyl, allyl, butenyl and pentenyl, aromatic hydrocarbon groups such as phenyl and benzyl, and alicyclic hydrocarbon groups such as cyclohexyl. The 2 functional groups (R) may also form a crosslinkage.

As shown in FIG. 2, the aromatic condensation compounds (aromatic condensation molecules) of formula (1) may have a portion of the aromatic nucleus reduced, and such compounds are also within the scope of the present invention. Compounds with the aromatic portion reduced such as shown in FIG. 2 may also be obtained by reducing the compounds of FIG. 1, but as will be explained later, they may be easily obtained by adjusting the reaction conditions for synthesis of the compounds of formula (1) according to the invention.

The aromatic compounds of the invention represented by formula (1) may have at least one of the 2 nitrogen atoms in quaternary form. Here, the anion as the quaternary salt counter is typically chlorine ion, iodine ion, perchlorine ion, boron tetrafluoride ion, etc. These quaternary salts become soluble in water and are particularly suitable for evaluating interaction with biological substances such as DNA.

The aromatic condensation compounds of the invention are obtained by condensation reaction of N,N'-diphenyl-p-phenylenediamine with a carboxylic acid in an amount of at least 2 molar equivalents, usually 5–10 molar equivalents, with respect to the diamine, in the presence of a Lewis acid (see FIG. 3). The carboxylic acid used is determined by the R of the aromatic condensation compound represented by formula (1) and may be, for example, acetic acid (R: methyl) propionic acid (R: ethyl), butyric acid (R: propyl) benzoic acid (R: benzyl), etc. When the two functional groups (R) in the molecule of formula (1) are different, N,N'-diphenyl-p-phenylenediamine is reacted with a carboxylic acid in an amount of at least 1 molar equivalent with respect to the diamine in the presence of a Lewis acid, the product where R had bound to only one site of the 2 reaction points of the diamine is first isolated, and then a carboxylic acid with a different functional group (R) than the first is used for reaction with the product in the same manner as above.

A variety of Lewis acids (catalysts) may be used, the most preferred being zinc chloride (ZnCl2). Zinc chloride is generally used in a proportion of 10–15 molar equivalents with respect to the N,N'-diphenyl-p-phenylenediamine.

The reaction proceeds by heating to a temperature of 180–210° C. The reaction time is generally from 3 to 7 hours. Surprisingly, the present inventors have found that by adjusting the reaction conditions it is possible to vary the conjugate property of the resulting product. That is, when the excess carboxylic acid is completely removed during the reaction to raise the reaction temperature to 210° C., a compound with a portion of the aromatic nucleus reduced such as shown in FIG. 2 is obtained. In contrast, when a low reaction temperature (190° C.) is maintained without removing the excess carboxylic acid during the reaction, an aromatic condensation compound such as shown in FIG. 1 can be obtained.

To obtain a quaternary product, it may be reacted by stirring with methyl iodide in the absence of a solvent.

The aromatic condensation compounds of the invention obtained by the method described above were confirmed to exist as a pair of enantiomers with optical activity due to twisting. Also, since the aromatic condensation compounds of the invention have a conjugated aromatic nucleus, they have a characteristic absorbance zone in the ultraviolet/visible region and also fluorescence in the visible region. The compounds shown in FIG. 1 have particularly strong fluorescence due to their wide conjugated systems. Also, since the aromatic condensation compounds of the invention have two nitrogens (N) in the molecule, they can provide a coordination site for metals. In addition, the aromatic condensation compounds of the invention are generally soluble in organic solvents such as methanol, ethanol, benzene and chloroform, and their quaternary salts are soluble in polar solvents such as water, methanol, ethanol, dimethylformamide and dimethylsulfoxide (especially water), and are therefore advantageous for various uses, exemplified by those mentioned below.

Because the aromatic condensation compounds of the invention form a pair of enantiomers due to the twisting of the molecules, they are believed to be useful as a novel type of optically active building block. For example, since the aromatic condensation compounds of the invention have nitrogen atoms (N) as the metal coordination sites in the molecule, they may be expected to give asymmetric coordinated compounds with metals and thus provide new metal catalysts for asymmetric reactions.

Also, by oxidation-reduction reaction, the compounds represented in FIG. 1 can be easily converted into compounds represented in FIG. 2, and the compounds represented in FIG. 2 can be easily converted into compounds represented in FIG. 1. In other words, the aromatic condensation compounds of the invention shown in FIG. 1 could be used as asymmetric oxidation reagents, while the aromatic condensation compounds of the invention shown in FIG. 2 could be used as asymmetric reduction reagents.

Furthermore, the aromatic condensation compounds of the invention are also expected to be useful as nucleating reagents and pharmaceuticals because they include an acridine structure. Acridine derivatives are known as intercalators into nucleic acid double helixes, such as DNA; for example, intercalation into tumor cell DNA destroys the 3-dimensional structure of the DNA, thus impeding its proliferation and acting as an anti-tumor agent. The interaction between acridine derivatives and nucleic acids is the π-π attraction between the π electrons of the condensed aromatic nucleus of acridine and the π electrons of the nucleic acid residue, but the molecules of the invention having a larger π plane than acridine can be expected to applicable as new intercalators in not only nucleic acid double-helixes but also triple-helixes.

Because the aromatic condensation molecules of the invention exist in a right-handed twisted form (P form) and a left-handed twisted form (M form), they can be expected to accomplish specific intercalation into nucleic acids with right-handed helixes and left-handed helixes. The strong fluorescence of the aromatic condensation molecules of the invention can be applied for common fluorescent agents as well as for clear indicators of the positions where the molecules are intercalated in nucleic acids.

EXAMPLES

The present invention will now be explained by way of the following examples in order to more clearly demonstrate the features of the invention; these examples, however, are in no way intended to restrict the invention.

Example 1
Synthesis of 13,14-dimethyl dibenzo[b,j][4,7] phenanthroline 13,14-dimethyl dibenzo[b,j][4,7]phenanthroline, wherein there two Rs in FIG. 1 are methyl, was synthesized in the following manner.

Into a 3-necked flask equipped with a cooling tube and stirring apparatus there were added 3.58 g (14 mmol) of N,N'-diphenyl-p-phenylenediamine, 5.0 ml (86 mmol) of acetic acid and 20.0 g (150 mmol) of zinc chloride, and the mixture was heated to 180° C. with a mantle heater while stirring with the stirring apparatus. When a temperature of 180° C. was reached the cooling tube was switched to a distillation apparatus and a portion of the excess acetic acid was distilled off. The reaction temperature was raised to 190° C. and heated stirring was continued for 5 hours. Ammonia was added to the 3-necked flask while the reaction mixture was still hot, for neutralization of the excess zinc chloride. The brown precipitate produced by this process was filtered, dried and then extracted with chloroform using a Soxhlet extractor. The extracted solution was heated and then concentrated under reduced pressure. The concentrate was separated by column chromatography (filler: alumina, eluent: chloroform), and there was recovered the component with Rf value of 0.6 as inspected by thin-layer chromatography (solid layer: alumina, developer: chloroform). The solvent was removed from the component by heating and reduced pressure, and the resulting yellow crystals were recrystallized with a benzene-petroleum benzine mixed solvent to obtain yellow needle-like crystals. The purified yield was 2.41 g (56%). The following analysis data confirmed that the desired product had been obtained.

Product Identification Data

Melting point: 217–218° C.
$^1$H-NMR (ppm, CDCl$_3$): 2.82 (6H, s, methyl), 7.70 (2H, t, aromatic nucleus positions 2,11), 7.85 (2H, t, aromatic nucleus positions 3,10), 7.85 (2H, s, aromatic nucleus positions 6,7), 8.23 (2H, w, aromatic nucleus positions 1,12), 8.27 (2H, w, aromatic nucleus positions 4,9).
$^{13}$C-NMR (ppm, CDCl$_3$): 19.5 (methyl), 123.2, 124.5, 126.5, 126.7, 129.6, 129.8, 133.7, 142.2, 146.8, 150.5 (aromatic nucleus).
Mass spectrometry: m/e 308 (theoretical value: 308).

Example 2
Synthesis of 13,14-dimethyl-6,7 dihydrodibenzo[b,j][4,7] phenanthroline 13,14-dimethyl-6,7 dihydrodibenzo[b,j][4,7] phenanthroline, wherein there two Rs in FIG. 2 are methyl, was synthesized in the following manner.

Into a 3-necked flask equipped with a cooling tube and stirring apparatus there were added 3.58 g (14 mmol) of N,N'-diphenyl-p-phenylenediamine, 5.0 ml (186 mmol) of acetic acid and 20.0 g (150 mmol) of zinc chloride, and the mixture was heated to 180° C. with a mantle heater while stirring with the stirring apparatus. When a temperature of 180° C. was reached the cooling tube was switched to a distillation apparatus and a portion of the excess acetic acid was distilled off. The reaction temperature was raised to 210° C. by completely removing the acetic acid, and heated stirring was continued for 5 hours. Ammonia water was added to the 3-necked flask while the reaction mixture was still hot, for neutralization of the excess zinc chloride. The brown precipitate produced by this process was filtered, dried and then extracted with chloroform using a Soxhlet extractor. The extracted solution was heated and then concentrated under reduced pressure. The concentrate was separated by column chromatography (filler: alumina, eluent: chloroform), and there was recovered the component with Rf value of 0.25 as inspected by thinlayer chromatography (solid layer: alumina, developer: chloroform). The solvent was removed from the component by heating and reduced pressure, and the resulting white crystals were recrystallized with a benzene-petroleum benzine mixed solvent to obtain white needle-like crystals. The purified yield was 60 mg (5.6%). The following analysis data confirmed that the desired product had been obtained.

Product Identification Data
Melting point: sublimation at 222–223° C.
$^1$H-NMR (ppm, CDCl$_3$): 2.56 (6H, s, methyl), 3.1–3.5 (4H, m, —CH$_2$CH$_2$—), 7.59 (2H, t, aromatic nucleus positions 2,11), 7.75 (2H, t, aromatic nucleus positions 3,10), 8.08 (4H, w, aromatic nucleus positions 1,4,9,12).
$^{13}$C-NMR (ppm, CDCl$_3$): 17.5 (methyl), 34.4 (—CH$_2$CH$_2$—), 124.4, 126.1, 126.3, 127.7, 129.0, 129.5, 141.6, 146.1, 161.7 aromatic nucleus).
Mass spectrometry: m/e 310 (theoretical value: 310).

Example 3
Confirmation of Enantiomers 13,14-dimethyl dibenzo[b,j][4,7]phenanthroline which was synthesized in Example 1 was examined for intermolecular energy barriers by molecular force field calculation (force field: MM2), and upon calculating the free energy of the most stable structure of the molecule by molecular orbital calculation (MOPAC), it was predicted to give a pair of enantiomers based on molecular twisting. According to molecular force field calculation, the free energy barrier of the racemization between the enantiomers can be estimated to be at least about 100 kJ/mol, which is believed to allow their separation at normal temperature. Monocrystals of the product of Example 1 were therefore prepared and subjected to X-ray structural analysis, while optical resolution was also attempted by high-performance liquid chromatography.

Preparation and X-ray Structural Analysis of Monocrystals

A 20 mg amount of the product of Example 1 dissolved in 2 ml of benzene solution was placed in a Pyrex test tube with an inner diameter of 7 mm and a length of 170 mm. After slowly adding 2 ml of petroleum benzine so as not to disturb the surface of the test tube, it was sealed and allowed to stand in a cool, dark area. After about 2 days, yellow crystals of a few square millimeters precipitated on the surface. These were filtered and used as a sample for monocrystal X-ray analysis.

Figure 6:
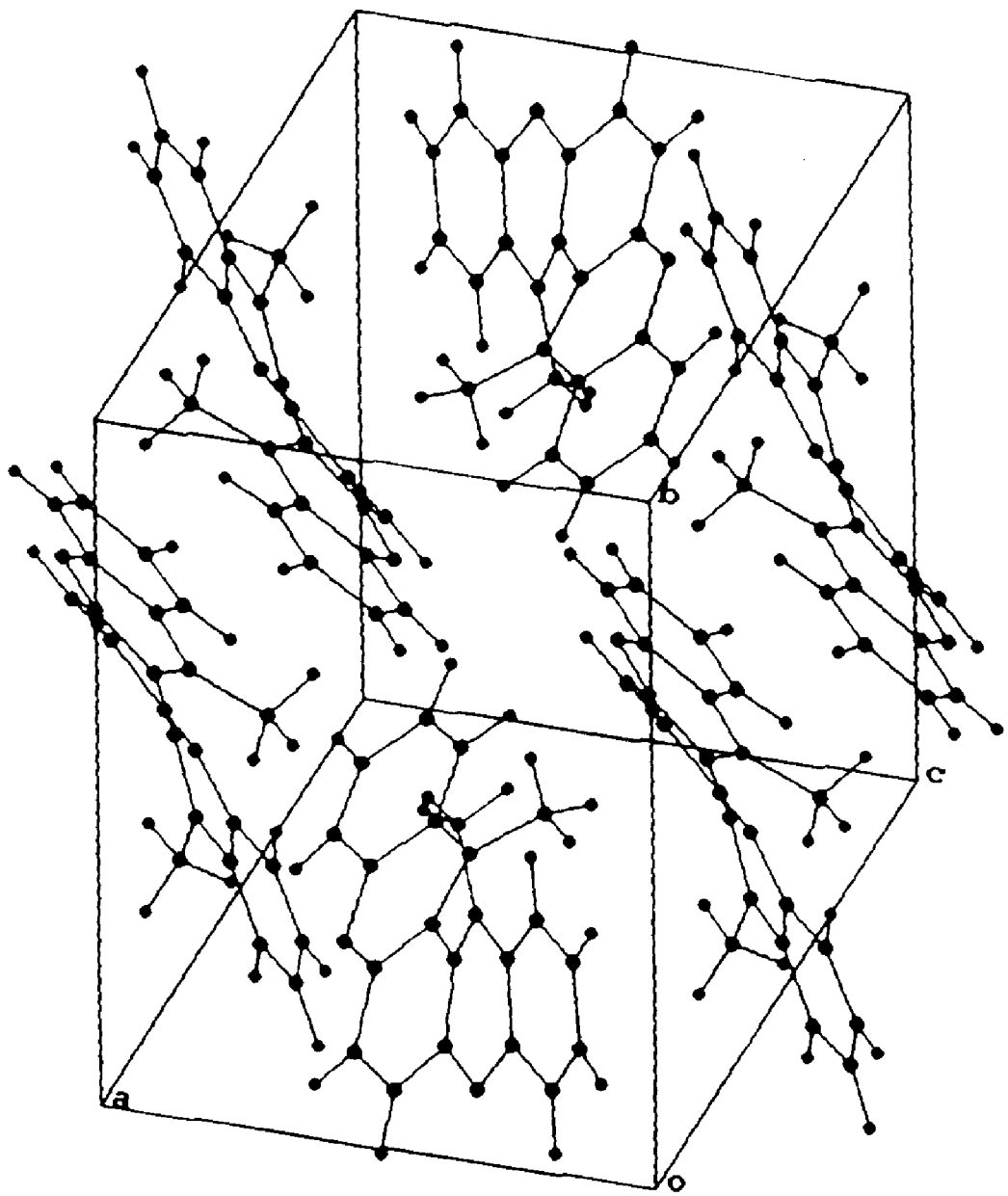
FIG. 6 is an illustration showing the unit cell of an aromatic condensation compound according to the invention based on X-ray structural analysis.

As a result of the structural analysis, it was shown that the 13,14-dimethyl dibenzo[b,j][4,7]phenanthroline of Example 1 had twisting of the aromatic nucleus (FIG. 4), matching the results of molecular orbital calculation, and exists as a pair of enantiomers due to the twisting (FIG. 5). It was shown that each unit cell contains 6 such molecules, with right-handed and left-handed helixes alternating each 3 molecules (see FIG. 6).

Optical Resolution by High-performance Liquid Chromatography

A 1 μl volume of a saturated acetonitrile solution of the product of Example 1 was separated by high-performance liquid chromatography under the conditions described below, upon which the enantiomers exhibited 2 completely separated signals (retention time: 63.7 minutes and 83.8 minutes).

Column: Shiseido RU-2
Eluent: acetonitrile/diethylamine=99/1 (vol %)
Flow rate: 0.25 ml/min
Pressure: 31 kg/cm$^2$
Detector: ultraviolet detector (275 nm)

It was thus confirmed that the aromatic condensation compounds of the present invention form a pair of stable enantiomers due to molecular twisting.

In the examples described above, the reagents and solvents were used without purification, unless otherwise specified. Also, the silica gel for the thin-layer chromatography was Silica Gel 60 by Merck Co. and the alumina for the thin-layer chromatography was Aluminum Oxide 60 (Type E) by Merck Co. The silica gel for the column chromatography was Silica Gel 60 (230–400 mesh) by Merck Co., and the alumina was Aluminum Oxide 90 active, neutral (activity I) by Merck Co. The melting point was measured with an MP-S3 melting point pyrometer by Yanagimoto Co.

The $^1$H and $^{13}$C nuclear magnetic resonance spectrum (NMR) was measured with a JNM-270 ($^1$H resonance frequency: 270 MHz) by Nihon Denshi Co. The mass spectrum was measured without a matrix, using a Voyager RP time-of-flight mass analyzer by PerSeptive Co. The high-performance liquid chromatography was carried out using 880 series and Gulliver series products of Nihon Spectrometry Co. The columns used were a Wakosil 5C18 reverse phase column for general analysis by Wako Junyaku Industries, and an RU-2 optical activation column by Shiseido Co. The X-ray structural analysis of the monocrystals was carried out using an AFC7r monocrystal structure analyzer by Rigaku Co. The molecular force field calculation (force field: MM2) for determination of the energy barrier between enantiomers and the molecular orbital calculation (MOPAC) for determination of the most stable structure were accomplished using CAChe software (Version 3.8) by Sony Tectronics Co.

What is claimed is:

1. An aromatic condensation compound represented by the following general formula (1):

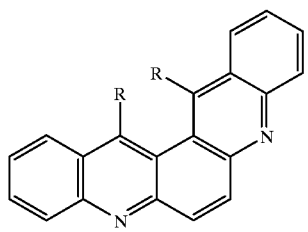

(1)

wherein each R is the same or a different functional group and selected from among hydrogen and linear, branched and cyclic hydrocarbon groups of 1–16 carbon atoms, wherein each R may not be hydrogen at the same time, said aromatic condensation compound being present as right-handed (R) and left-handed (S) enantiomeric isomers.

2. An aromatic condensation compound according to claim 1, wherein part of the aromatic nucleus is reduced.

3. An aromatic condensation compound according to claim 1, wherein at least one of the two nitrogens is quaternary.

4. An aromatic condensation compound according to claim 2, wherein at least one of the two nitrogens is quaternary.

5. A process for producing an aromatic condensation compound according to claim 1, which comprises heating and reacting N,N'-diphenyl-p-phenylenediamine with a carboxylic acid represented by the general formula —RCOOH, wherein R is selected from hydrogen and linear, branched and cyclic hydrocarbon groups of 1–16 carbon atoms, in an amount of at least 2 molar equivalents with respect to said diamine, at 180–210° C. in the presence of Lewis acid wherein the reaction is susceptible to a Lewis acid.

6. A process of claim 5, wherein the Lewis acid is zinc chloride.

7. A process of claim 5, wherein the excess carboxylic acid is completely removed during the reaction to increase the reaction temperature to 210° C.

8. A process of claim 6, wherein the excess carboxylic acid is completely removed during the reaction to increase the reaction temperature to 210° C.

9. A process of claim 5, wherein the reaction temperature is kept at 190° C. without removing the excess carboxylic acid during the reaction.

10. A process of claim 6, wherein the reaction temperature is kept at 190° C. without removing the excess carboxylic acid during the reaction.

* * * * *